(12) United States Patent
Weissman et al.

(10) Patent No.: US 6,506,562 B1
(45) Date of Patent: Jan. 14, 2003

(54) ALLELE FREQUENCY DIFFERENCES METHOD FOR PHENOTYPE CLONING

(75) Inventors: Sherman M. Weissman, New Haven, CT (US); Jon J. Jonsson, Revkiavik (IE)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/427,104

(22) Filed: Oct. 26, 1999

Related U.S. Application Data (60) Provisional application No. 60/105,667, filed on Oct. 26, 1998.

(51) Int. Cl.$^7$ .......................... C07H 21/04; C12Q 1/68
(52) U.S. Cl. .......................... 435/6; 435/91.2; 536/23.1
(58) Field of Search .................... 435/6, 91.2; 536/23.1

(56) References Cited

U.S. PATENT DOCUMENTS

| | | | |
|---|---|---|---|
| 5,057,410 A | * 10/1991 | Kawasaki et al. | 435/6 |
| 5,459,039 A | 10/1995 | Modrich et al. | |
| 5,556,750 A | 9/1996 | Modrich et al. | |
| 5,679,522 A | 10/1997 | Modrich et al. | |
| 5,759,822 A | * 6/1998 | Cehnchik et al. | 435/91.2 |
| 5,804,382 A | 9/1998 | Sytkowski et al. | |
| 5,830,655 A | * 11/1998 | Monforte et al. | 435/6 |
| 5,928,872 A | * 7/1999 | Lin et al. | 435/6 |

OTHER PUBLICATIONS

Meese et al. "Alu–PCR: Characterization of a chromosome 6 specific hybrid mapping panel and cloning of chromosome–specific markers" Genomics, vol. 12, p. 549–554, 1992.*
New England Biolabs Catalog 1996, "Adaptors", p. 115.*
Patel et al "A novel and rapid method of risolating sequences adjacent to rare cutting sites and their use in Physical mapping" Nucleic Acids Research, vol. 19, No. 16, p. 4371–4375, 1991.*
Nelson et al "Genomic mismatch scanning: a new approach to genetic linkage mapping" Nature Genetics, vol. 4, p. 11–18, May 1993.*
Lizardi et al. "Mutation detection and single–molecule counting using isothermal rolling–circle amplification" Nature Genetics, vol. 19, Jul. 1998, pp. 225–232.
Bloom et al. "Fidelity of *Escherichia coli* DNA Polymerase III Holoenzyme" The Journal of Biological Chemistry vol. 272, No. 44 Oct. 31, 1997, pp. 27919–27930.
Cheung et al. "Linkage–disequilibrium mapping without genotyping" Nature Genetics, vol. 13, Mar. 1993, pp. 225–230.
Prashar et al. "Analysis of differential gene expression by display of 3' end restriction fragments of cDNAs" Proc. Natl. Acad. Sci.. USA vol. 93, pp. 659–663 Jan. 1996.
Hingorani et al. "Toroidal proteins: Rinning rings round DNA" Current Biology, vol. 8, No. 3, 1998 pp. R83–R86.
Ferrin et al. "Long–range mapping of gaps and telomers RecA–assisted restriction endonuclease (RARE) cleavage" Nature Genetics, vol. 6, Apr. 1994, pp. 379–383.
Kelman et al. "Processivity of DNA polymerases: two mechanisms, one goal" Structure 1998, vol. 6, No. 2, pp. 121–125.
Ferrin et al. "Selective Cleavage of Human DNA: RecA–Assisted Restriction Endonuclease (RARE) Cleavage", Science, vol. 254, Dec. 6, 1991, pp. 1493–1497.
Geschwind et al. "A biotinylated MutS fusion protein and its use in a rapid mutation screening technique" Genetic Analysis: Biomolecular Engeinnering 13 (1996) 105–11.
Abstract submitted to the American Society of Human Genetics Meeting 1996 Date of submission: Jun. 7, 1996.

* cited by examiner

*Primary Examiner*—W. Gary Jones
*Assistant Examiner*—Jeanine Goldberg
(74) *Attorney, Agent, or Firm*—Banner & Witcoff, Ltd.

(57) ABSTRACT

A general method is described for screening cDNAs, genes or genome segments to directly isolate and characterize sequences associated with particular phenotypes. In the case of the human genome, a simplification of the starting material is needed, and a specific method to generate highly polymorphic genome subsets for this purpose is presented. The general screening method identifies DNA sequences containing allele frequency differences when groups with dissimilar phenotypes are compared. The approach is based on mathematical principles of inequality. A change in the abundance ratio of homoduplexes of perfectly matched sequences to heteroduplexes of perfectly matched sequences, or, conversely, of mismatched homoduplexes to mismatched heteroduplexes, serves as an indicator of allele frequency difference.

27 Claims, 4 Drawing Sheets

```
                            SEQUENCE LISTING (1) GENERAL INFORMATION:

(iii) NUMBER OF SEQUENCES: 7

(2) INFORMATION FOR SEQ ID NO: 1

(i) SEQUENCE CHARACTERISTICS:
            (A) LENGTH: 27 residues
            (B) TYPE: nucleic acid
            (C) STRANDEDNESS: single
            (D) TOPOLOGY: linear (ii) MOLECULE TYPE: <Unknown>
            (A) DESCRIPTION: DNA (xi) SEQUENCE DESCRIPTION: SEQ ID NO: 1:

GGGCGACAGA GCGAAGACTC CGTCTCA                                          27

(2) INFORMATION FOR SEQ ID NO: 2

(i) SEQUENCE CHARACTERISTICS:
            (A) LENGTH: 27 residues
            (B) TYPE: nucleic acid
            (C) STRANDEDNESS: single
            (D) TOPOLOGY: linear (ii) MOLECULE TYPE: <Unknown>
            (A) DESCRIPTION: DNA (xi) SEQUENCE DESCRIPTION: SEQ ID NO: 2:

GGGCGACAGC AGCGAGACTC CGTCTCA                                          27

(2) INFORMATION FOR SEQ ID NO: 3

(i) SEQUENCE CHARACTERISTICS:
            (A) LENGTH: 27 residues
            (B) TYPE: nucleic acid
            (C) STRANDEDNESS: single
            (D) TOPOLOGY: linear (ii) MOLECULE TYPE: <Unknown>
            (A) DESCRIPTION: DNA (xi) SEQUENCE DESCRIPTION: SEQ ID NO: 3:

GGGCGACAGC AGCGAGACTC TGTCTCA                                          27

(2) INFORMATION FOR SEQ ID NO: 4
```

```
    (i) SEQUENCE CHARACTERISTICS:
        (A) LENGTH: 32 residues
        (B) TYPE: nucleic acid
        (C) STRANDEDNESS: single
        (D) TOPOLOGY: linear (ii) MOLECULE TYPE: <Unknown>
        (A) DESCRIPTION: DNA (xi) SEQUENCE DESCRIPTION: SEQ ID NO: 4:

TCTGGACCAC TGTACGATGA TATGTCACCG AG                                32

(2) INFORMATION FOR SEQ ID NO: 5

(i) SEQUENCE CHARACTERISTICS:
        (A) LENGTH: 11 residues
        (B) TYPE: nucleic acid
        (C) STRANDEDNESS: single
        (D) TOPOLOGY: linear (ii) MOLECULE TYPE: <Unknown>
        (A) DESCRIPTION: DNA (xi) SEQUENCE DESCRIPTION: SEQ ID NO: 5:

GATCCTCGGT G                                                       11

(2) INFORMATION FOR SEQ ID NO: 6

(i) SEQUENCE CHARACTERISTICS:
        (A) LENGTH: 24 residues
        (B) TYPE: nucleic acid
        (C) STRANDEDNESS: single
        (D) TOPOLOGY: linear (ii) MOLECULE TYPE: <Unknown>
        (A) DESCRIPTION: DNA (xi) SEQUENCE DESCRIPTION: SEQ ID NO: 6:

TCTGGACCAC TGTACGATGA TATG                                         24

(2) INFORMATION FOR SEQ ID NO: 7

(i) SEQUENCE CHARACTERISTICS:
        (A) LENGTH: 26 residues
        (B) TYPE: nucleic acid
        (C) STRANDEDNESS: single
        (D) TOPOLOGY: linear (ii) MOLECULE TYPE: <Unknown>
        (A) DESCRIPTION: DNA (xi) SEQUENCE DESCRIPTION: SEQ ID NO: 7:

GGGCGACAGA GCGAGACTCC GTCTCA                                       26
```

ALLELE FREQUENCY DIFFERENCES METHOD FOR PHENOTYPE CLONING

This application claims the benefit of co-pending provisional application Serial No. 60/105,667, filed Oct. 26, 1998, which is expressly incorporated herein in its entirety.

The invention was made with partial government support under NCI grant CA42556. The government has certain rights in the invention.

A general method is described for screening cDNAs, genes or genome segments to directly isolate and characterize sequences associated with particular phenotypes. In the case of the human genome, a simplification of the starting material is needed, and a specific method to generate highly polymorphic genome subsets for this purpose is presented. The general screening method identifies DNA sequences containing allele frequency differences when groups with dissimilar phenotypes are compared. The approach is based on mathematical principles of inequality. A change in the abundance ratio of homoduplexes of perfectly matched sequences to heteroduplexes of perfectly matched sequences, or, conversely, of mismatched homoduplexes to mismatched heteroduplexes, serves as an indicator of allele frequency difference.

TECHNICAL FIELD

This invention relates to screening complex reannealed DNA preparations to identify sequences exhibiting differences in allele frequency when phenotypically different groups are compared. The DNA material can originate from genes, genomes, or cDNA. For human applications, simplification of genomic DNA is needed, and a way to generate genome subsets is described. Genome subsets generated in this manner are enriched for polymorphic sequences and sufficiently reduced in complexity to allow reannealing, a prerequisite for the invention.

BACKGROUND OF THE INVENTION

Most common diseases of humans are not inherited as single gene traits but rather result from complex interactions between one or several genes and the environment. Current methods of identifying disease genes under these circumstances are inefficient and this is one of the major limitations of modern medical genetics. Promising methods for identifying genes affecting complex diseases are affected relative analysis, linkage disequilibrium analysis and association studies. All require genotyping a very high density of markers for genome-wide search making these methods impractical for use with current genotyping techniques (1–3). These requirements make it difficult to rapidly identify genes affecting complex diseases.

The term "phenotype cloning" was developed to describe the isolation of genes by virtue of their effect and without requiring prior knowledge of their bio-chemical function or map position (4). Phenotype cloning methods are based on inferences about characteristics of the unknown gene(s), and these characteristics then form the basis to directly isolate the gene in question. As an excellent example, of inferences which can be made about disease genes to allow their direct isolation is the prediction that somatic mutations in tumors will sometimes result in the loss or generation of genoric restriction fragments. A method called representational difference analysis (RDA) has been developed by combining genomic representation, subtractive enrichment, and kinetic enrichment to detect short restriction fragments present in a "target" genome but not in another "driver" genome (5). This method has been used to directly isolate genetic elements associated with tumor formation (6). In addition, RDA has been used to detect autosomal recessive loci in F2 progeny from crossing two inbred strains of laboratory mice (7), but it lacks sufficient power to isolate fragments associated with inherited traits in outbred humans.

A second example of phenotype cloning which would have many important applications, especially in identifying genes in linkage disequilibrium and hence genes affecting complex diseases, is the direct isolation of genomic sequences that are identical-by-descent (IBD) in a group of patients with the same disease. Sanda and Ford outlined the genetic basis for such methods in the case of autosomal dominant disease (8). They pointed out that genomic segments from two unrelated individuals should contain sequence differences due to polymorphisms. In contrast, IBD sequences, that two relatives have in common, would be identical since the mutation rate in humans is very low. Lastly, segregation and recombination result in genomic IBD sequences among relatives becoming fewer and shorter with increasing number of meiosis separating the individuals. IBD sequences shared by distant relatives affected with the same genetic disease should therefore contain the disease gene.

Figure 1:
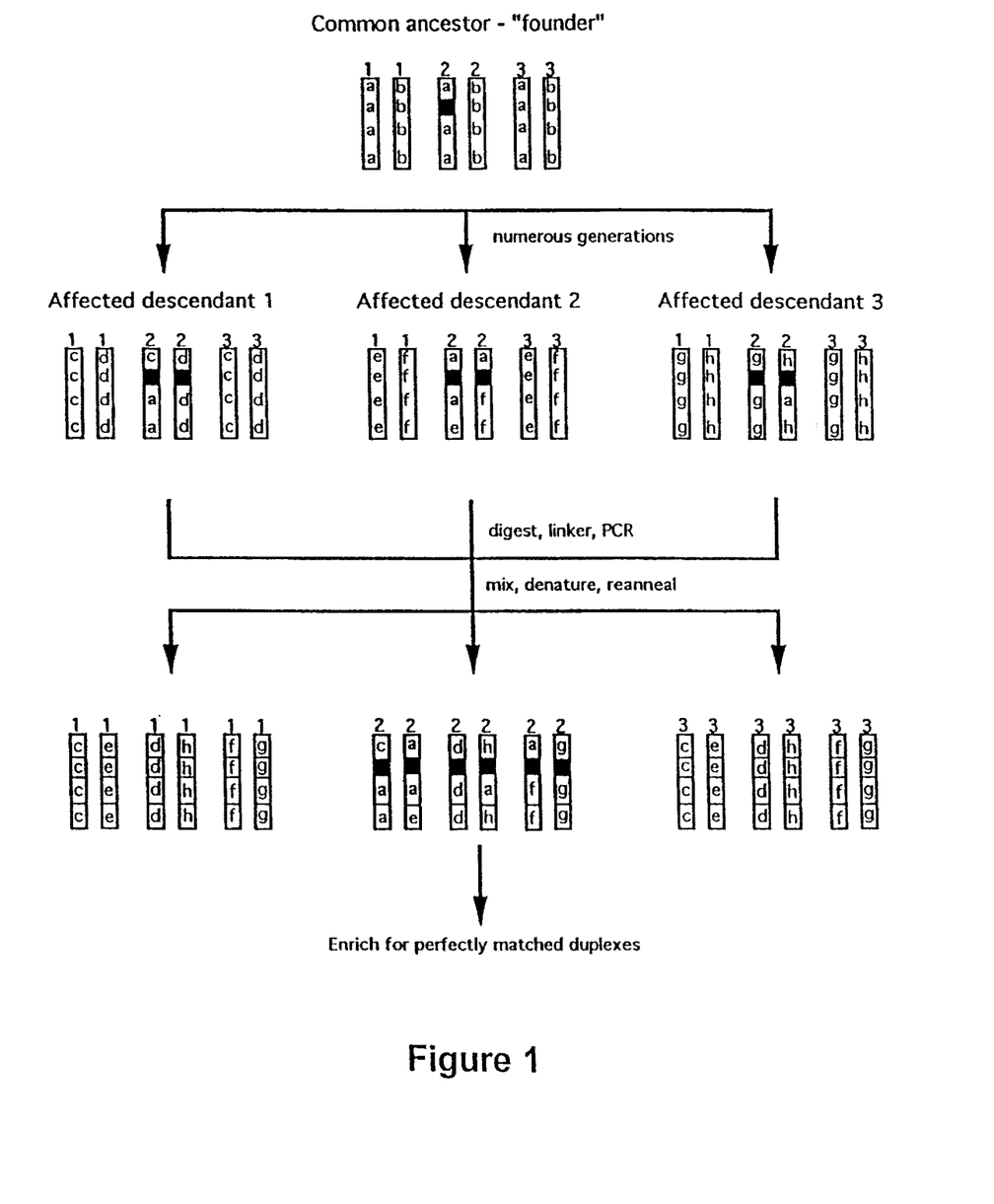
FIG. 1 is a diagrammatic representation of identical-by-descent sequences in autosomal recessive diseases observed in small, relatively homogeneous populations that have an unusually high frequency of disease.

An example where isolation of IBD sequences could be used to identify disease genes is in autosomal recessive disease if the patients come from a small, isolated, homogeneous population, and the disease is unusually frequent in the population. In that setting one can assume that there is a founder effect and that the disease gene is IBD (FIG. 1). A common reason why disease genes are in linkage disequilibrium is that they are IBD, so an extension of this approach might allow identification of genes in linkage disequilibrium that are affecting common complex diseases in isolated homogenous populations. However, not all patients with complex diseases would be homozygous for the disease gene. Rather patients would be more likely to be heterozygotes or homozygotes for a gene predisposing to disease and conversely less likely to carry genes conveying a protective effect. Methods capable of detecting quantitative differences in allele frequencies, i.e., allele frequency difference between patients and normal controls therefore is essential in studying genetics of complex disease.

In 1993 Nelson and associates described "genomic mismatch scanning" method to directly identify IBD sequences in yeast (9). They used _S. cerevisiae_ hybrids as a model system and showed that sequences shared by two independently generated hybrids from the same parent strains could be identified in many instances. Experiments of this kind are much easier to do in yeast than humans. The yeast genome is 250 times simpler than the human genome, it contains far fewer repetitive sequences, and genomic sequences of two yeast strains differ more than genomes of unrelated humans. It has thus far not been possible to do comparable experiments with human genomic DNA. In order to do so one needs to use methods to reproducibly generate simplified but highly polymorphic representations of the human genome. Pooling techniques based on the mathematical principles outlined below are also essential to identify IBD sequences as well as other sequences showing AFD.

The human genome is enormously long $3 \times 10^9$ base pairs and it is far too complex for efficient reannealing of homologous DNA strands after denaturation. The rate of annealing of a mixture of nucleic acid fragments in liquid phase is inversely proportional to their complexity. Efforts have therefore been made to generate simplified representations of the genome for genetic methods based on cross hybridization of homologous sequences from different genomes. The exact degree of simplification of human genomic DNA needed to achieve efficient annealing depends on the conditions of hybridization including total DNA concentration, hybridization buffer, and temperature. In general a 10–100 fold simplification is needed for efficient annealing to occur at high DNA concentrations in high salt aqueous solutions (5).

Ideal representations for cross hybridizations studies on human material should therefore be at least 10–100 fold simplification of genomic DNA. They should contain sequences representing many thousands of different loci that are evenly distributed throughout the genome. In addition, the representations should be enriched for highly polymorphic sequences to facilitate genetic studies. Lastly, one should be able to easily and reproducibly generate equivalent representations from genomes of different individuals.

SUMMARY OF THE INVENTION

It is an object of the invention to provide highly polymorphic representations of the human genome.

It is another object of the invention to provide a widely applicable method for phenotype cloning based on allele frequency differences.

These and other objects are accomplished by the present invention, which provides genomic DNA fragments that are enriched for polymorphic sequences and sufficiently reduced in overall complexity to permit effective reannealing of homologous segments so that they can be used in detecting allele frequency differences as well as in genomic mismatch scanning. In a typical method of the invention, DNA sequences in cDNAs, genes or genomic segments are screened to isolate and characterize sequences associated with particular phenotypes by comparing the abundance of homoduplexes of perfectly matched sequences in the sample with heteroduplexes of perfectly matched sequences, or comparing the abundance of mismatched homoduplexes in the sample with mismatched heteroduplexes. As described hereafter, other genomic subsets are also suitable for allele frequency difference screening.

In the practice of a method of the invention DNA sequences from complex DNA sample pools, where allele frequency differs between the pools, are identified by mixing at least two different complex DNA samples together to generate a pool, annealing specific adaptors to DNA fragments in the pools, removing excess adaptors that are not ligated to the DNA fragments, mixing at least two different pools together, denaturing the mixed pools of DNA samples, reannealing the denatured pools of DNA samples to obtain DNA duplexes containing homologous strands, separating perfectly matched DNA duplexes in the pools from duplexes containing mismatched base pairs or insertion/deletion loops, and selectively amplifying either perfectly matched or mismatched DNA homoduplexes and heteroduplexes.

In one embodiment, a highly polymorphic subset of human genome DNA is generated by (a) digesting a genomic DNA sample with a restriction enzyme to obtain genomic DNA fragments; (b) ligating adaptors capable of binding to ends of the genomic fragments; (c) removing excess adaptors that are not ligated to genomic DNA fragments obtained in step (b); (d) subjecting the genomic DNA-adaptor preparation so produced to a controllable initiating reaction for a PCR reaction in the presence of a DNA primer complementary to the consensus sequence for the 3' end of Alu repeat sequences in the sample, and then a PCR amplification with Alu 3' end primer and 5' adaptor primer; (e) digesting the products produced in the amplification reaction of step (d) with restriction enzymes with cognate sequences built into the primer sequences to generate DNA fragments with asymmetric overhangs; and (f) isolating DNA subsets exhibiting selectively amplified sequences flanking 3' ends of Alu repeats produced in step (e).

DETAILED DESCRIPTION OF THE INVENTION

This invention is based on the development of a method of phenotype cloning by screening complex DNA preparations for allele frequency differences. Toward that goal, it provides simplified yet highly polymorphic subsets of the human genome, and direct experimental isolation of disease genes by virtue of their effect alone, without requiring prior knowledge of their biochemical function or map position.

The method is based on inequality mathematical principles. It allows identification of sequences exhibiting allele frequency differences by denaturing and reannealing pools of complex DNA sequences from two populations, distinguishing perfectly matched and mismatched duplex DNA and selectively recovering homoduplexes and heteroduplexes. To reduce the complexity of human genomic DNA, genomic subsets are generated based on selective PCR amplification of A-rich sequences flanking 3' ends of Alu repeats, many of which are highly polymorphic. Allele frequency differences could be due to causative mutations or result from linkage disequilibrium and other close associations between the sequence and disease gene. As used herein, "polymorphism" refers to genetic sequence variation between different individuals of a species.

In one embodiment of the invention, a highly polymorphic subset of human genome DNA is generated by: (1) digesting a genomic DNA sample with a restriction enzyme to obtain genomic DNA fragments; (2) ligating adaptors capable of binding to ends of the genomic fragments; (3) removing excess adaptors that are not ligated to genomic DNA fragments obtained in step (2); (4) subjecting the genomic DNA-adaptor preparation so produced to a controllable initiating reaction for a PCR reaction in the presence of a DNA primer complementary to the consensus sequence for the 3' end of Alu repeat sequences in the sample, and then a PCR amplification with Alu 3' end primer and 5' adaptor primer; (5) digesting the products produced in the amplification reaction of step (4) with restriction enzymes with cognate sequences built into the primer sequences to generate DNA fragments with asymmetric over-hangs; and (6) isolating DNA subsets exhibiting selectively amplified sequences flanking 3' ends of Alu repeats produced in step (5). Other subsets may be generated by reannealing homologous segments of selectively amplified sequences obtained in step (6). As used herein, the word "homologous" means originating from the same location in the genome.

Examples are given in the next section. In some embodiments, the restriction enzyme employed to digest genomic DNA is an enzyme or enzymes that generate GATC 5' overhangs, e.g., Sau3AI, BstYI, and BamHI. As used herein, "complexity" refers to the number times the length of different sequences in a preparation. It is an advantage of the invention that the complexity of a subset generated as described herein can also be regulated by varying the annealing temperature during the initiating reaction, or by the recognition specifity of the restriction enzyme.

Example Alu 3' end primers useful in the practice of a method of the invention are GGGCGACAGAGCGAA-GACTCCGTCTCA (SEQ ID NO: 1), GGGCGACAG-CAGCGAGACTCCGTCTCA (SEQ ID NO: 2), and GGGCGACAGCAGCGAGACTCTGTCTCA (SEQ ID NO: 3); in some embodiments, the Alu 3' end primers have an extra base added to generate sites for type IIS restriction enzymes. Example adaptors are TCTGGACCACTGTAC-GATGATATGTCACCGAG (SEQ ID NO: 4) and GATCCTCGGTG-cordycepin (SEQ ID NO: 5) and a 5' adaptor primer is TCTGGACCACTGTACGATGATATG (SEQ ID NO: 6).

This invention thus provides material for a method of isolating DNA sequences from complex DNA sample pools, where allele frequency differs between the pools. Typical process steps include (a) mixing at least two different complex DNA samples together to generate a pool; (b) annealing specific adaptors to DNA fragments in the pools; (c) removing excess adaptors that are not ligated to the DNA fragments; (d) mixing at least two different pools together; (e) denaturing the mixed pools of DNA samples; (f) reannealing the denatured pools of DNA samples to obtain DNA duplexes containing homologous strands; (g) separating perfectly matched DNA duplexes in the pools from duplexes containing mismatched base pairs or insertion/deletion loops; and (h) selectively amplifying either perfectly matched or mismatched DNA homoduplexes and heteroduplexes.

In alternative embodiments, other genome subsets described in the literature could also be used for allele frequency difference screening, including complex DNA comprised of genes, genomic segments or cDNAs. These include preparations enriched for CA-repeats (18), IRE-PCR products (31), inter Alu PCR products (32), methods based on PCR amplification of individual loci followed by pooling of products, or other subsets of sufficiently reduced complexity to permit reannealing. In the case of non-human genomic work PCR products using other interspersed repeats in a comparable manner could be used.

As used herein, a homoduplex is double-stranded DNA where both strands derive from the same genome or pools of genome samples, and a heteroduplex is double-stranded DNA where each strand originated from different genomes or different pools of genomes. By "perfectly matched" is meant double-stranded DNA where each base residue is correctly paired with a base on the opposite strand, i.e., A to T and C to G. By "mismatched" is meant double-stranded DNA where at least one base residue on either strand is either not paired with any residue, or paired with an incorrect base, i.e., A not paired with T, C not paired with G.

The mixing, reannealing and selective amplification of mismatched or perfectly matched duplexes may be done separately for each pool. In some embodiments, mismatched duplexes generated in step (g) above are destroyed, such as, for example, by incubating the mismatched duplexes with an enzyme that cuts DNA containing mismatched DNA or insertion/deletion loops. In alternate embodiments, they are purified by affinity binding to proteins recognizing mismatched DNA, e.g., by use of mutS and/or mut Y and/or carboxy terminus of p53 and/or thymidine glycosylase as affinity proteins. Such affinity proteins can be derived from human, yeast, bacteria, especially $E.\ coli$, or other suitable source.

Heteroduplexes may be selectively amplified by cross-hybridizing two different genomes or genome pools, each containing fragments with 5' overhang adaptors and 3' adaptors, provided that the two most 3' nucleotides of the 3' adaptors are mismatched with regard to the 5' adaptors, and the 3' adaptors are methylated at specific residues to mediate resistance to digestion with specific restriction enzymes, to obtain a mixture; extending reannealed duplexes in the mixture with a 5' and 3' exo-free polymerase to generate primer binding sites at each end of the heteroduplexes but not homoduplexes; digesting with methylation-sensitive restriction enzymes to remove primer binding sites generated from duplexes not having 3' adaptors; and amplifying heteroduplexes by using primer adaptors for both ends of fragments with adaptor primers specific for each fragment end, originating from different pools of DNA. Example restriction enzymes are BbsI or BbvI for fragment ends generated by digestion of Alu 3' repeat primer sequences, and MboI, BstYI, and/or BamHI for ends generated by digestion of 5' adaptor sequences.

Homoduplexes may likewise be selectively amplified by cross-hybridizing two different genomes or genome pools, each containing fragments with 5' overhang adaptors and 3' adaptors, provided that the 3' adaptor anneals perfectly with the 5' adaptor on the homoduplex, the 3' adaptors do not match with 5' adaptors from the opposite genome or pools of genomes, and the 3' adaptors is methylated at specific residues to mediate resistance to restriction enzyme digestion; extending reannealed duplexes with a 5' and 3' exo-free polymerase to generate primer binding sites at each end of homoduplexes; digesting with methylation-sensitive restriction enzymes to remove primer binding sites generated from duplex DNA not having 3' adaptors; and amplifying homoduplexes by using 2 primer adaptors for both ends of fragments with adaptor primers specific for each fragment end, originating from the same genome preparation. Example restriction enzymes are BbsI or BbvI for fragment ends generated by digestion of Alu 3' repeat primer sequences and MboI, BstYI, and/or BamHI for ends generated by digestion of 5' adaptor sequences.

Amplified material may be further treated with methylases to mediate restriction to enzyme digestion. The materials are then mixed, denatured, and reannealed, and the perfectly matched and mismatched duplex DNA is separated; in some cases, the mismatched duplexes are destroyed. Homo- or hetero-duplex DNA can then be selectively recovered by PCR amplification based on resistance of primer binding sites to digestion by methylation sensitive restriction enzymes.

Recovered homo- and heteroduplexes so obtained can be labelled with different signals, pooled, and hybridized to arrayed libraries, arrayed libraries of selected subsets of genomic clones, or metaphase chromosomes.

The invention thus provides a variety of DNA preparations. Segments having allele frequency differences between the pools are detected by changes in signal ratio between homo- and heteroduplexes according to the principle of inequality.

The following examples are presented to further illustrate and explain the present invention and should not be taken as limiting in any regard.

EXAMPLES

The methods described herein can be used on genomic DNA or on cDNA as starting material. In the latter case the aim would be to identify cDNAs where there is a difference in sequence variation between patients and controls. This approach could then be used to identify genes affecting not only Mendelian diseases but also complex diseases where there is a significant difference in cDNA sequence. It would not matter what the cDNA mutation is, nor would all patients need to have the same mutation. The sequence variation could therefore be either causative mutations altering function of the genes or simple neutral polymorphisms in which case they would serve as genetic markers for the gene. Another essentially unsolved problem in medical genetics is identification of disease genes causing sporadic, often devastating, lethal phenotypes. These conditions are often due to new mutations in unknown genes. The patient generally has not reproduced or is incapable of doing so if the condition is genetic lethal. In this setting genetic analysis cannot be done since only a single case is present in each family (with rare exceptions). Methods using cDNA material could also be applied in that setting.

a) Generation of highly polymorphic representations of the human genome by selective amplification of Alu repeat 3' ends. A method to selectively amplify sequences flanking 3' ends of Alu repeats to generate a genome representation with the characteristics suitable for either identification of AFD (see below) or for GMS-type of methods was devised. There are greater than 500,000 Alu repeats dispersed throughout the human genome (10). Of special interest for our purpose is the high degree of polymorphism frequently present in sequences immediately flanking 3' ends of Alu repeats (11–13). These polymorphisms are generally either differences in number of short sequence repeats or length of the polyadenylated sequence at 3' ends of Alu repeats. The sequence differences are thought to arise primarily from polymerase slippage resulting in expansion or contraction of short repeated sequences (14).

Three 27 nucleotide long primers were designed to be complementary to the consensus sequence at the 3' end of Alu repeats (Table 1). In the primers, an extra base is added into the Alu consensus sequence to generate restriction sites for the type IIS (shifted) restriction enzymes BbsI and BbvI. This has the advantage that the inserted base is placed away from the 3' end of the primer at a position compatible with efficient amplification. Yet, after restriction digestion with the corresponding enzyme to remove the adaptor only a short piece of repetitive Alu sequence will remain at the end of each fragment, decreasing the risk of illegitimate hybridization of non-homologous sequences in subsequent steps. In addition, digestion with the type IIS enzymes gives an unique 4 bp 5' overhang, e.g., CGTC in the case of BbsI. Specific adaptors can therefore be ligated to PCR products generated with these primers. This overhang is different from the GATC 5' overhang of the genomic restriction site cut downstream of the Alu repeats. This difference allows separate adaptor sets to be ligated to each end of PCR products generated with this method. The asymmetric adaptors allow various approaches to selective amplification as outlined below.

TABLE 1

Alu Primers

| | |
|---|---|
| Alu repeat 3' end consensus: | GGGCGACAGAGCGA.GACTC CGTCTCA[1] |
| AluBbsI Primer | GGGCGACAGAGC<u>GAAGAC</u>TC\|CGTCTCA[2] |
| Alu repeat 3' end consensus: | GGGCGACAG.AGCGAGACTCC GTCTCA[3] |
| AluBbvIC Primer* | GGGCGACA<u>GCAGC</u>GAGACTCC\|GTCTCA[4] |
| AluBbvIT Primer* | GGGCGACA<u>GCAGC</u>GAGACTCT\|GTCTCA[5] |
| Adaptors | |
| SN32 | TCTGGACCACTGTACGATGATATGTCACCGAG[6] |
| SN24 | TCTGGACCACTGTACGATGATATG[7] |
| SN12A | GATCCTCGGTGX**[8] |

Recognition sequences are underlined. Vertical bars indicate sites of cleavage.
*These two primers differ in the 7th base from the 3' end; this base is highly variable among Alu repeats.
**= Terminal X is cordycepin.
[1]SEQ ID NO: 7
[2]SEQ ID NO: 1
[3]SEQ ID NO: 7
[4]SEQ ID NO: 2
[5]SEQ ID NO: 3
[6]SEQ ID NO: 4
[7]SEQ ID NO: 6
[8]SEQ ID NO: 5

Figure 2:
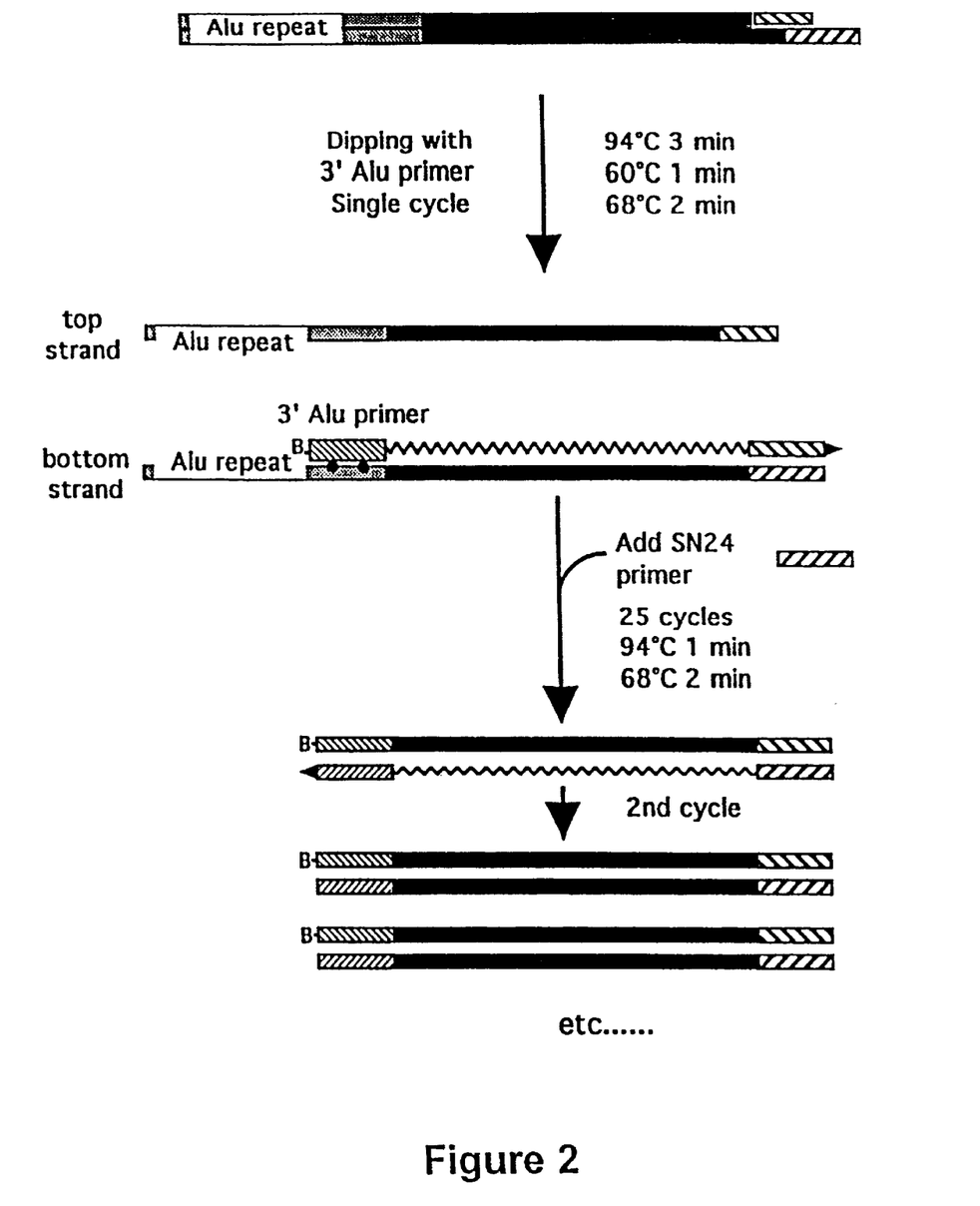
FIG. 2 is a representation illustrating selective amplification of Alu 3' flanks. The complexity and content of the DNA obtained can be adjusted as described hereafter.

The method involves digesting genomic DNA with a restriction enzyme leaving a 5' GATC overhang, e.g., Sau3AI. Subsequently adaptors SN32 and SN12A with 24 bp 5'overhang (Table 1) are ligated to the genomic fragments. This preparation is used as template for two sequential polymerase chain reactions (PCR) as outlined in FIG. 2. This strategy was performed on an experimental template, a 40 kb segment of human genomic DNA cloned in the cosmid pFC12 (15). This segment of genomic DNA contains the beta-globin locus and it has been completely sequenced and found to contain 6 Alu repeats. PCR was done using a 15:1 mixture of Klentaq polymerase and PfuI polymerase which contains 3' exonuclease proofreading activity. This combination of polymerases greatly reduces the rate of nucleotide misincorporation into nascent templates and it decreases the correlation between length of template and efficiency of PCR amplification (16). Selective amplification of Alu repeat 3' flanks from pFC12 was predicted to result in products differing in length from 130 to 1058 bp. Various temperatures for first cycle "initiating dipping reaction" were tested and the correlation between annealing temperature and number of different Alu repeat 3' flanks amplified was determined. For example, using the AMuBbsI primer and dipping at 40° C. three out of the six different Alu repeat 3' flanks were selectively amplified but at 60° C. only one of Alu repeat 3' flanks was amplified. The identity of PCR products as Alu repeat 3' flanks was confirmed by sequencing. A correlation between the degree of complementarity of primers to the 3' ends of Alu repeats and the efficiency of amplification was observed. For example, the best matching Alu repeat 3' flank was the only one that amplified after dipping at 60° C. Conversely, products representing 3' flanks of the Alu repeats that matched most poorly with the primers were never seen. Incomplete reaction controls using just one primer alone did not result in significant background if 3' OH ends of Sau3AI fragments were blocked with the SN12A adaptor containing a non-extendible cordycepin residue at the 3' end (Table 1).

The Alu repeat 3' flank representation was cloned into lambda gt10 vector and a library containing 2.5 million phage characterized further. Complexity studies suggested that on the order of 100,000 Alu repeat 3' flanks are amplified from total human genomic DNA if initial dipping at 60° C. was used. This is in agreement with the experiments using pFC12 and results in overall sequence complexity of the Alu repeat 3' flank presentation being on the order of 1% of the genome. Sequence analysis of 60 inserts and flanking sequence analysis on 4 random inserts was consistent with that the vast majority of amplified material represented Alu 3' flanks. One of four randomly chosen Alu repeat 3' flanks from the preparation was highly polymorphic confirming that the representation was greatly enriched for highly polymorphic loci.

One powerful feature of this approach is that the overall complexity of the representation can be easily varied in straightforward ways. The frequency of restriction sites in the initial digestion of DNA can be changed by using either Sau3AI (recognition sequence GATC), BstYI (RGATCY) or BamHI (GGATCC). Going from the more frequent cutter Sau3AI (1:318 bp) to BamHI (1:5534 bp) (17), the average length of amplified flanks increases but the number of flanks amplified decreases as increasing number of flanks have the restriction site too far away for efficient amplification to occur. Secondly, by varying the initial "dipping" temperature in PCR (FIG. 2) the complexity can be adjusted. Higher temperatures result in more stringent amplification, fewer flanks amplified, and therefore simpler representations. In addition, by making slight changes in the Alu primer sequence (for instance by adding a base at the 3' end) different populations of Alu repeat 3' flanks can be amplified. The capability of adjusting complexity and content of the Alu repeat 3' flank populations makes the technique much more versatile since it is expected that the optimal number and type of Alu repeat 3' flanks in the representation would be variable depending on the application. Genetic variables affecting optimal complexity include number of patients and controls available, length and degree of linkage disequilibrium of the disease gene in the study subjects as well as the difference in frequency of the disease gene in patients versus controls. In addition, experimental variables such as hybridization conditions, methods to separate mismatched from perfectly matched DNA and homo- and heteroduplexes would all bear on the optimal complexity of the representation.

The selective amplification of Alu repeat 3' ends therefore generates material with characteristics highly suitable for AFD or GMS-type methods. Previously a method to select for CA repeats and therefore presumably highly polymorphic sequences was described from this laboratory (18). This method is, however, much more technically demanding than the Alu repeat 3' flank method. In particular, reproducible generation of equivalent representations from different individuals would be difficult to achieve in part because of the complexity of the procedure but also because efficiency of enrichment correlates with the length of the CA repeat present Different alleles would therefore not be enriched for in equal manner using that method. However, this method as well as other published methods in the literature could serve as subsets for AFD screening (31, 32).

b) Identification of sequences containing allele frequency distortion (AFD); a general approach based on inequality mathematical principles for direct enrichment of polymorphic sequences in linkage disequilibrium or closely associated with disease genes. A general approach to directly identify polymorphic loci in the genome for which the frequency of specific alleles is different between groups of individuals for instance patients and control groups was developed. This difference in frequency can be due to linkage disequilibrium or result from close genetic association of polymorphic alleles with the disease gene(s) in question. The methods collectively called allele frequency difference (AHD) identification, are based on taking genome representations from a group of patients (a genomes) and unaffected controls (b genomes) mixing them together, denaturing and letting them anneal. If $a_{ij}$ and $b_{ij}$ are the fraction of haploid genome representations a and b carrying the jth allele at the ith locus then according to the inequality principle:

$$(a_{ij}-b_{ij})^2 > 0 \text{ if } a_{ij} \neq b_{ij}, \text{ else wise} = 0 \quad (1)$$

therefore $$a_{ij}^2 + b_{ij}^2 > 2 \cdot a_{ij} b_{ij} \text{ if } a_{ij} \neq b_{ij}, \text{ else wise equal} \quad (2)$$

and $$\sum_j a_{ij}^2 + \sum_k b_{ik}^2 \geq 2 \cdot \sum_l a_{il} b_{il} \quad (3)$$

This relationship can be used experimentally by destroying mismatches and then selectively amplifying either a and b homoduplexes or ab heteroduplexes. Following specific amplification $a_{ij}^2 + b_{ij}^2$ homoduplexes (labeled with red fluorescent tag) or $a_{ij}b_{ij}$ heteroduplexes (labeled with green tag) can be hybridized to arrayed clones (PACs, YACs, etc.) or metaphase chromosomes. and ratios of red to green signals compared to identify areas where $a_{ij} \neq b_{ij}$. Instead of fluorescent signals one could also label with other techniques for instance by using different radioisotopes.

It is important to appreciate the advantage of this approach to AFD identification over the more simple method of mixing each pool separately. denaturing, reannealing and recovering perfectly matched duplex DNA. In both of those pools there would be variation in how polymorphic each genomic fragment is (with many not being polymorphic at all) and in recovery of intact duplexes. PCR products of each pool after amplification of perfectly matched DNA would therefore contain widely different concentrations of various genome segments. But there should not be a difference in relative abundance of corresponding PCR products in the two pools except where polymorphic alleles are more often identical, i.e., less polymorphic, in one of the pools. In other words, the locus needs to have a different degree of polymorphism in the patient pool versus the control pool for it to be detected. Such would be the case in the limited situation where one is studying an autosomal recessive disease in an isolated population as previously explained (FIG. 1). In that situation there should be no or minimal polymorphism in the patient group at loci closely linked to the disease gene whereas they should be polymorphic in randomly chosen controls. However, the "anneal separately" approach would not work well when studying complex diseases where the expectation is that there might be one or more alleles of a gene increasing susceptibility to disease and conversely one or several alleles protecting against the disease at the same or other loci. Each of these alleles might be in linkage disequilibrium with a unique haplotype consisting of specific alleles at closely linked polymorphic loci such as Alu repeat 3' flanks. This might be because of a founder effect or from some other genetic association.

A major limitation of the "anneal separately" approach is that it is only sensitive to differences in degree of polymorphism at a locus but not to frequency differences of specific alleles. One need only consider the simple situation where a disease causing allele e1 at a diallelic locus x has 95% frequency in patients but where a protective allele e2 has 95% frequency in healthy controls. This locus would not give a signal using the "anneal separately" approach since there is no difference in degree of polymorphism in patient group versus healthy controls! In contrast AFD methods based on the inequality principle, i.e., mixing of genomes a and b together and than comparing abundance of recovered $a^2+b^2$ homoduplexes with the ab heteroduplexes would detect any differences in specific allele frequencies at polymorphic loci between groups of patients and healthy controls. It does not matter whether loci are more or less polymorphic in the patient population versus controls only that there is a quantitative difference in representation of specific alleles between the two groups compared. The difference can be due to linkage disequilibrium affecting the phenotype or from other causes. The AFD identification approach should work regardless of whether there are one or multiple haplotypes associated with the disease gene or whether there are one or more haplotypes containing a protective gene. The only requirement is that there is a difference in the frequency of specific alleles between patients and controls. This is an essential attribute of a method aimed at studying the genetics of complex disease. Of note is that the power of detecting genes by the AFD approach would be greatest in detecting haplotypes that are rare in one group but increased in frequency in the comparison group or vice versa when a very common haplotype is decreased in frequency in comparison group. Greater changes in frequency of haplotypes are needed for detection as the frequency of the haplotype approaches 50% in the populations studied.

In addition, methods based on AFD identification allow for integration of signals from several different but linked loci if labeled PCR products are hybridized to YACs or PACs containing these same loci or even whole chromosomes. For each locus where there is a difference in allele frequency between patients and controls one would get a enhanced signal from homoduplexes relative to heteroduplexes regardless of the nature of the difference (equation 3). This would s necessarily be the case with the "anneal separately" approach. Consider for example a YAC containing 2 diallelic loci g and h and tightly linked gene d containing either a disease allele d1 or protective allele d2. The disease allele d1 arose on two different haplotypes g1-h1-d1 and g1-h2-d1 which are present of equal frequency in patient population. The protective alleles are similarly associated with haplotypes g1-h2-d2 and g2-h2-d2. In the "mix separately" approach locus g would be relatively enriched in the patient population but the h locus in the healthy controls. However, since both hybridize to the same YAC or chromosome region the signals would cancel each other out. In the "anneal separately" approach one can therefore have either additive effect or canceling of signals from different loci but in methods based on AFD identification all loci where there is any difference in specific allele frequencies would give additive signals. The AHD identification is therefore much more powerful than the "anneal separately" strategy both in terms of detecting differences in allele frequencies at individual loci as well as resulting in integration of signals from separate loci.

Figure 3:
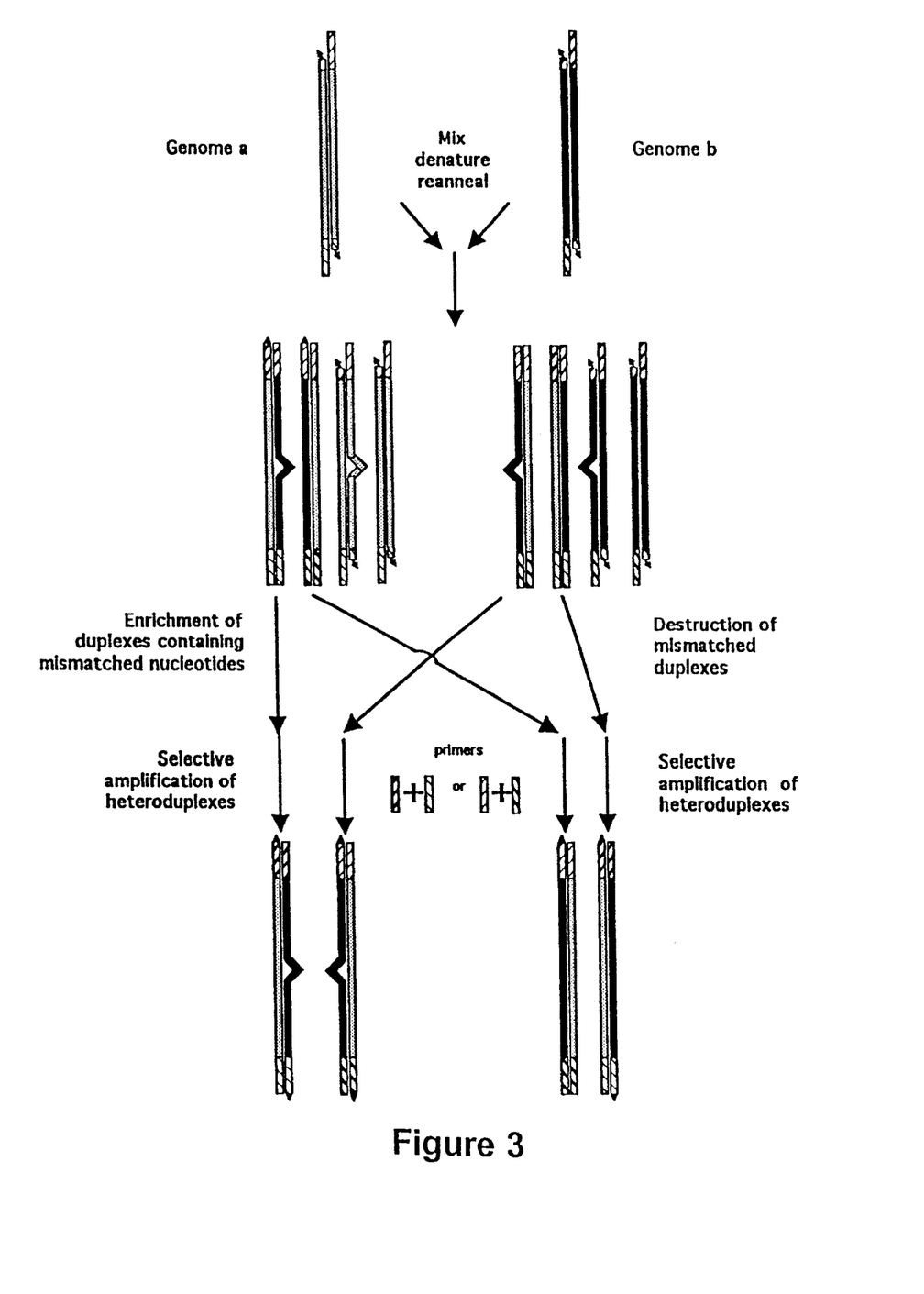
FIG. 3 is a representation illustrating amplification of heteroduplexes with asymmetrical adapters.

After annealing of DNA, the next step in the laboratory procedure is separation of mismatch-free duplexes from duplexes containing mismatched base pairs or insertion/deletion loops (FIG. 3). As outlined above, this separation can be achieved by either destroying or selectively retaining mismatched duplex DNA. Destruction of mismatched DNA can be done with the MutHLS system as described in the literature (9) if GATC sequences on one strand are dam methylated (this could include hemimethylating adaptor DNA at the A residue). Other endonucleases capable of recognizing mismatched for single-stranded DNA could also be used (4). Nucleases that recognize loop of single stranded DNA such as mung bean nuclease and S1 nuclease (21) could be used since a large fraction of Alu repeat 3' flank polymorphism involve differences in number of short sequence repeats recognizable by those nucleases (11–14).

However, destruction of mismatches must be nearly complete for the above approach to work. Therefore, it may be more effective in certain situations to selectively retain duplexes containing mismatches where even a low recovery, if specific, is sufficient. Inherent in this approach is also general enrichment for sequences representing polymorphic loci at the expense of sequences from non-polymorphic loci. In this setting, the following considerations are important:

$$\sum_j a_{ij} = \sum_j b_{ij} = 1 \quad \text{because one or another allele at each locus is present in each individual} \quad (4)$$

therefore $$\left(\sum_j a_{ij} - \sum_j b_{ij}\right)^2 = 0 \quad \text{for every } i \quad (5)$$

subtract equation (3) above from (5):

$$\sum_{\substack{j,k \\ (j \neq k)}} (a_{ij}a_{ik}) + \sum_{\substack{j,k \\ (j \neq k)}} (b_{ij}b_{ik}) \leq \sum_{\substack{j,k \\ (j \neq k)}} (a_{ij}b_{ik}) \quad (6)$$

Therefore, selective amplification of hybrids between different alleles at a locus also gives a red green ratio that is constant except at loci where the two samples differ in allele frequency, in which case the heteroduplexes are always reduced compared to homoduplexes.

Selective retention of mismatched double stranded DNA from a mixture containing both perfectly matched and mismatched DNA can be achieved by using proteins involved in mismatch repair or maintenance of genome integrity. Examples from the literature include MutS protein of *E. coli* (22) as well as its homologs in eukaryotic cells such as yeast MSH1 (23) the carboxy-terminus of protein p53 (24), and thymidine glycosylase.

Regardless of whether destruction or selective isolation of mismatched duplexes is applied the difference in abundance of homologous sequences between $a^2+b^2$ homoduplexes and ab heteroduplexes can be amplified by taking the pools and reannealing them separately followed by reamplification of homologous annealed sequences. This kinetic enrichment should square the preexisting differences in abundance.

Figure 4:
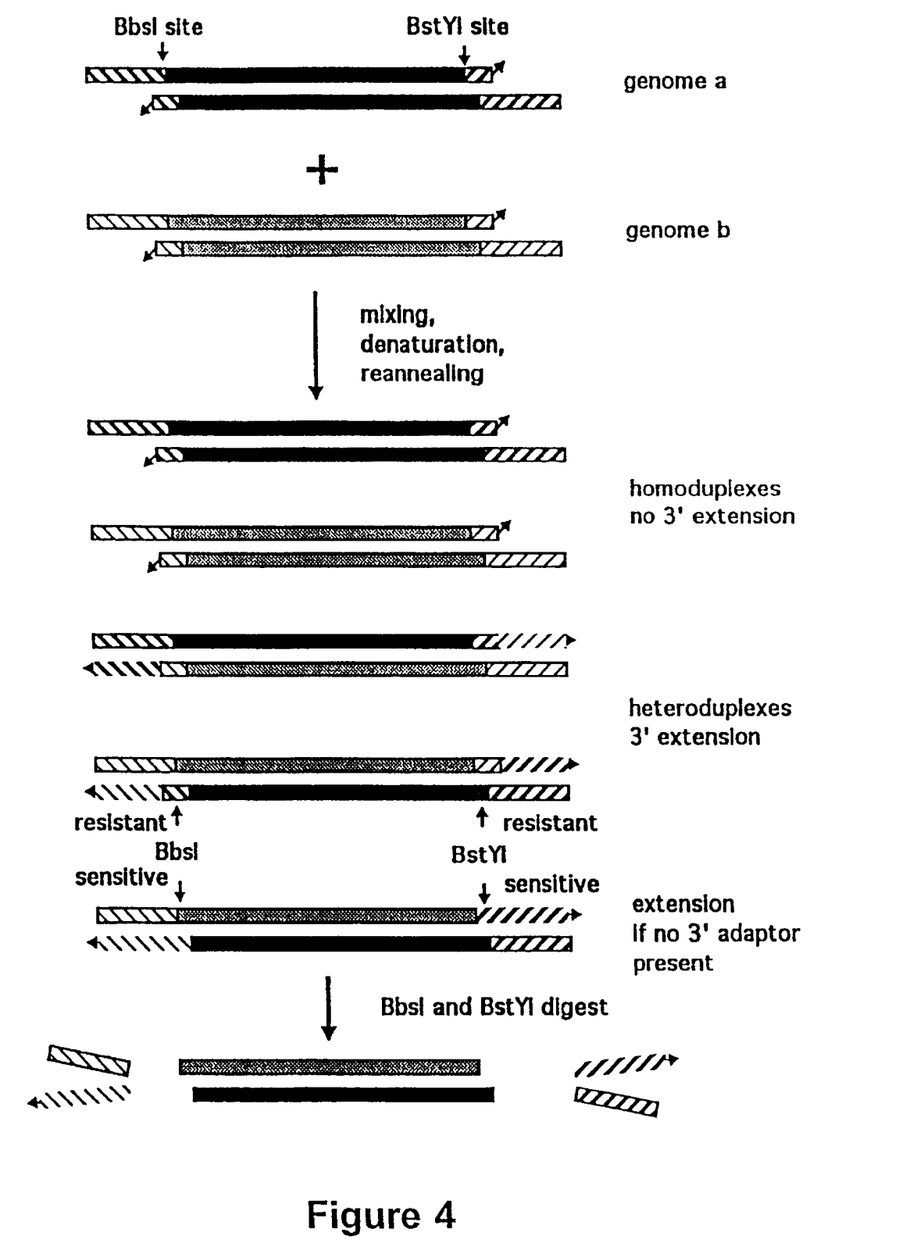
FIG. 4 is a representation illustrating selective amplification by using sequence divergence and hemimethylation on the 3' adapters.

Recently there has been significant progress in using linkage methods in studying genetics of complex disease. A major limitation is as previously stated that a very high number of markers need to be typed for a genome wide scan. It was therefore only in recent years that genes affecting complex diseases were first mapped by genome wide search (25). Efforts to streamline genotyping of a very high number of loci have centered on using pooling strategies. PCR products representing several different loci from the same patient can be pooled and run in the same lane of a sizing gel if the products are well separated in terms of size and also by using multicolor labeling with fluorescent dyes. Pooling can be taken one step further by pooling DNA from groups of patients and controls before genotyping. This approach is based on the correlation between densities of individual alleles on the genotyping tracing and frequency of the alleles in the group of individuals comprising the pool (26, 27). Despite these technological advances a genome wide scan with thousands or even tens of thousands of markers would still be a very formidable undertaking. In one sense the method of the invention is based on taking the concept of pooling still one step further in that the actual genotyping of all loci is done in the same reaction in a single tube, i.e., all genotyping is pooled. This approach allows for much more rapid genotyping of thousands or even tens of thousands loci. In addition, it is to be expected that diverse genes affect complex diseases and that the same genes do not always contribute to disease in all patients. In that case there could be associations between what genes are affecting the phenotype and various patient specific characteristics including clinical and laboratory criteria, population of origin, etc. Studies to detect disease genes will therefore typically involve repeated redefinition of patient and control pools based on different partitioning criteria and then searching for allele frequency distortion between different sets of pool pairs. This would be much more efficiently done using AFD identification by the method of the invention than using current genotyping techniques.

c) Selective amplification of homo- or heteroduplex DNA following separation of perfectly matched and mismatched double stranded DNA. As explained in section b it is imperative to have the ability to selectively amplify either homoduplexes from genomes a and b or ab heteroduplexes as the case may be (FIG. 3). The methods described in sections a) and b) would be applicable regardless of how this selective amplification is achieved. Methods to achieve this based on sequence divergence and hemimethylation on 3' adaptor pieces were devised (FIG. 4, the example given is selective amplification of heteroduplexes but the same strategy can be applied to selective amplification of homoduplexes by using different combinations of adaptor pairs). 5' overhang adaptors are used where the short adaptor binding to 3' end of fragments is 5' phosphorylated and contains 2 nucleotides at its 3' end that are mismatched with respect to its partner adaptor molecule that binds to the 5' end of the fragment. This 3' adaptor is, in contrast, completely matched with the 5' adaptor ligated to fragments from the cross-hybridizing genome (FIG. 4). Hybridization of two different genomes or genome pools is followed by extension with a 5' and 3' exo-free polymerase to generate primer binding sites at each end of heteroduplex molecules. To further ensure minimal amplification of homoduplexes, the 3' adaptors contain methylated bases mediating resistance to digestion with the restriction enzymes BbsI and BstYI (as an example of a GATC overhang enzyme used originally to cut the genome) which recognize sites built into adaptor stem. This step eliminates background amplification of duplexes with primer binding sites generated by extension of a minor population of duplexes that had adaptors only ligated to their 5' end but not the 3' end and therefore could be extended with the 5' and 3' exo-free polymerase. Selective amplification is then accomplished using primers corresponding to 5' sequences of BbsI adaptor from one genome and BstYI adaptor from the other genome. This use of end-specific primers further ensures selective amplification but it is not essential. The same approach would work using symmetric primers when overhangs at each end of the fragments and therefore the adaptors are identical. If the goal is to amplify homoduplexes then the adaptor sets ligated on fragments would contain adaptors that are completely matched but divergent with respect to adaptors on the other genome. Primers for PCR would similarly be chosen to separately amplify from the annealed mixture sequences originating from either genome a and b.

Alternatively, selective amplification of either heteroduplexes or homoduplexes from a reannealed mixture of nucleic acids can be accomplished from the same solution of reannealed DNA, using the same primers for either type of DNA. This scheme is useful as it avoids any variation in annealing between two different reactions, any variations in adapter ligation prior to annealing, or any variation in selective amplification because of the use of different primers.

In this scheme, adapters containing the same nucleotide sequence are ligated to both ends of all the DNA fragments in each of two pools (e.g., pool A and pool B). The adapters on pool A and pool B differ in the presence and position of methylated bases that block cutting by restriction enzymes when and only when the methylated base falls within the restriction enzyme recognition site. One embodiment employs two restriction sites on the adapters, one of which is methylated on the top strand and the other on the bottom strand. For the right restriction enzyme such as Alu, methylation of one strand prevents cutting of either strand. The primer binding sites for PCR are located externally to the restriction site (that is, the restriction site on the ligated adapter lies between the primer binding site and the attached DNA fragment from the pool). If site one of pool A is methylated on the top strand and site two on the bottom strand, while in pool B site one is methylated on the bottom strand and site two on the top strand, then after reannealing those duplexes where both strands are derived from the same pool will be protected from cutting. On the other hand, those duplexes formed with one strand from each of the two pools will have one site doubly protected and the other site unprotected. As a result, if the duplexes are cut with the restriction enzymes before amplification, only homoduplexes will be amplified. Conversely, if both strands of site one are methylated in one pool and both strands of site two in the other pool, only heteroduplexes will be amplified. Two different restriction sites are then used to either amplify only homo- or only heteroduplexes, depending on which restriction enzyme is used for cutting before amplification.

The procedure may be diagrammed as follows:

```
Adapter for pool A:

top strand              -(PCR primer binding
                         site)^mAGCTAGCT-(DNA insert)
bottom strand           -(PCR primer binding
                         site)TCGATCG^mA-(DNA insert)
Adapter for pool B:

top strand              -(PCR primer binding
                         site)AGCT_mAGCT-(DNA insert)
bottom strand           -(PCR primer binding
site)TCG^mATCGA-(DNA
insert)
Heteroduplex            -(PCR primer binding
                         site)^mAGCTAGCT-(DNA insert)
                        -(PCR primer binding
                         site)TCG^mATCGA-(DNA insert)
```

Note that the second AGCT on the heteroduplex is not methylated on either strand. The same is true for the reciprocal heteroduplex.

Finally, if one wants to pre-amplify by PCR before denaturing and reannealing the two pools, then only one of the two strands of the amplified product contains the chemically synthesized primer whose methyl group is inserted at the time of synthesis. To get selective methylation of a site on the opposite strand, an overlapping restriction site and methylase specific for that site is used.

d) Application of this technology to isolate cDNAs containing mutations or sequence variation. The principles and technology explained in sections b and c can also by applied to cDNA preparations with the aim of identifying significant sequence differences in patient cDNA preparations versus control DNA. Important in this regard is that comparable cDNA preparations be obtained from both patients and controls. Controls would include parents when a new mutation is suspected.

As described in the literature, cDNA can, for instance, be generated using a modified Gubler-Hoffman method (28) with oligo(dT) primers containing G, C, or A as the most 3' residue to ensure selective priming at the very 5' end of the poly-A tail (29). In addition, a heel containing a specific restriction site can be added to the primer to allow addition of asymmetric adaptors to the preparation at a later stage. The AFD method could be applied to full length cDNA as well as to cDNA restriction fragments generated by cutting cDNA preparations with a series of different restriction enzymes either between 5' or 3' adaptors and internal site or between two internal sites. In this regard it is especially interesting that untranslated regions of cDNA tend to be polymorphic so cDNA fragments including those regions would be of special interest. If need be, the cDNA preparation can be normalized (30) prior to AFD procedure. Subsequent to the AFD procedure, cDNAs where the ratio between $a^2$ and $b^2$ homoduplexes as well as ab heteroduplexes is different would be identified by hybridization to cDNA libraries or arrayed cDNA.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

REFERENCES

1. Lander E S, Schork N J. Genetic dissection of complex traits. Science 1994; 265:2037–48.
2. Kruglyak L, Lander E S. Complete multipoint sib-pair analysis of qualitative and quantitative traits. American Journal of Human Genetics 1995; 57:439–54.
3. Risch N, Merikangas K. The future of genetic studies of complex human diseases. Science 1996; 273:1516–7.
4. Jonsson J J, Weissman S M. From mutation mapping to phenotype cloning. Proceedings of the National Academy of Sciences USA 1995; 92:83–85.
5. Lisitsyn N, Lisitsyn N, Wigler M. Cloning the differences between two complex genomes. Science 1993; 259:946–951.
6. Lisitsyn N A, Lisitsina N M, Dalbagni G, et al. Comparative genomic analysis of tumors: Detection of DNA losses and amplification. Proceedings of the National Academy of Sciences USA 1995; 92:151–155.
7. Lisitsyn N A, Segre J A, Kusumi K, Lisitsyn N M, Nadeau J H, Frankel W N, Wigler M H, Lander E S. Direct isolation of polymorphic markers linked to a trait by genetically directed representational difference analysis. Nature Genetics 1994; 6:57–63.
8. Sanda A I, Ford J P. Genomic analysis I: inheritance units and genetic selection in the rapid discovery of locus linked DNA markers. Nucleic Acids Research 1986; 14:7265–7283.
9. Nelson S F, McCusker J H. Sander M A, Kee Y, Modrich P, Brown P O. Genomic mismatch scanning: a new approach to genetic linkage mapping. Nature Genetics 1993; 4:11–18.
10. Deininger P L. SINEs: short interspersed repeated DNA elements in higher eucaryotes. In: Berg D E, Howe M M (eds) Mobile DNA. Am Soc Microbiol 1989, pp. 619–36.
11. Economou E P, Bergen A W, Warren A C, Antonarakis S E. The polyadenylate tract of Alu repetitive elements is polymorphic in the human genome. Proceedings of the National Academy of Sciences USA 1990; 87:2951–2954.
12. Epstein N, Nahor O, Silver J. The 3' ends of Alu repeats are highly polymorphic. Nucleic Acids Research 1990; 18:4634.
13. Zuliani G, Hobbs H H. A high frequency of length polymorphism in repeated sequences adjacent to Alu sequences. American Journal of Human Genetics 1990; 46:963–969.
14. Arcot S S, Wang Z, Weber J L, Deininger P L, Batzer M A. Alu repeats: A source for the genesis of primate microsatellites. Genomics 1995; 29:136–44.
15. Collins F S, Stoeckert C J, Sedjeant G R, Forget B G, Weissman S M. GγB+Hereditary persistence of fetal hemoglobin: Cosmid cloning and identification of a specific mutation 5' to the Gγ gene. Proceedings of the National Academy of Sciences USA 1984; 81:4894–4898.
16. Barnes W M. PCR amplification of up to 35-kb DNA with high fidelity and high yield from lambda bacteriophage templates. Proceedings of the National Academy of Sciences USA 1994; 91:2216–2220.
17. Bishop D T, Williamson J A, Skolnick M H. A model for restriction fragment length distributions. American Journal of Human Genetics 1983; 35:795–815.
18. Kandpal R P, Kandpal G, Weissman S M. Construction of libraries enriched for sequence repeats and jumping clones, and hybridization selection for region-specific markers. Proceedings of the National Academy of Sciences USA 1994; 91:88–92.
19. Youil R, Kemper B W, Cotton, G H. Screening for mutations by enzyme mismatch cleavage with T4 endonuclease VII. Proceedings of the National Academy of Sciences USA 1995; 92:87–91.
20. Mashal R D, Koontz J, Sklar J. Detection of mutations by cleavage of DNA heteroduplexes with bacteriophage resolvases. Nature Genetics 1995; 9:177–183.
21. Eun H M. Enzymology primer for recombinant DNA technology. 1996. Academic Press, pp. 204–215.
22. Wagner R, Debbie P, Radman M. Mutation detection using immobilized mismatch binding protein (MutS). Nucleic Acids Research 1995; 23:3944–8.
23. Chi N W, Kolodner R D. Purification and characterization of MSH1, a yeast mitochondrial protein that binds to DNA mismatches. Journal of Biological Chemistry 1994; 269:29984–92.

24. Reed M, Woelker B, Wang P, Wang Y, Anderson M E, Tegtmeyer P. The C-terminal domain of p53 recognizes DNA damaged by ionizing radiation. Proceedings of the National Academy of Sciences USA 1995; 92:9455–9.
25. Sheffield V C, Nishimura D Y, Stone E M. Novel approaches to linkage mapping. Current Opinion in Genetics and Development 1995; 5:335–41.
26. Pacek P, Sajantila A, Syvanen A C. Determination of allele frequencies at loci with length polymorphism by quantitative analysis of DNA amplified form pooled samples. PCR Methods and Applications 1993; 2:313–7.
27. Khatib H, Darvasi A, Plotski Y, Soller M. Determining relative microsatellite allele frequencies in pooled DNA samples. PCR Methods and Applications 1994; 4:13–8.
28. Gubler U, Hoffman B J. A simple and very efficient method for generating cDNA libraries. Gene 1983; 25:263–9.
29. Borson N D, Salo W L, Drewes L R. A lock-docking oligo(dT) primer for 5' and 3' RACE PCR. PCR Methods and Applications 1992; 2:144–8.
30. Patanjali S R, Parimoo S, Weissman S M. Construction of a uniform-abundance (normalized) cDNA library. Proceedings of the National Academy of Sciences USA 1991; 88:1943–7.
31. Munroe D J, Haas M, Bric E, et al. IRE-bubble PCR: A rapid method for efficient and representative amplification of human genomic DNA sequences from complex sources. Genomics 1994; 19:506–514.
32. Kass D H, Batzer M A. Inter-Alu polymerase chain reaction: Advancements and applications. Anal Biochem 1995; 228:185–93.

The papers cited above are expressly incorporated herein in their entireties by reference.

What is claimed is:

1. A method for isolating and characterizing a sequence associated with a phenotype in a sample consisting of cDNAs, genes, or genomic segments of at least two groups of individuals which differ in the phenotype, comprising:

comparing abundance of perfectly matched homoduplex DNA in the sample with perfectly matched heteroduplex DNA in the sample, or comparing abundance of mismatched homoduplex DNA in the sample with mismatched heteroduplex DNA in the sample;

detecting a difference in abundance of perfectly matched homoduplex DNA from abundance of perfectly matched heteroduplex DNA in the sample or detecting a difference in abundance of mismatched homoduplex DNA from abundance of mismatched heteroduplex DNA in the sample, wherein a difference in abundance indicates the presence of a sequence in the sample which is present at different frequencies in the at least two groups of individuals; and identifying the sequence in the sample which is present at different frequencies in the at least two groups of individuals, said sequence being associated with the phenotype.

2. A method for generating a highly polymorphic subset of human genomic DNA which comprises:

(a) digesting a genomic DNA sample with a first restriction enzyme to obtain genomic DNA fragments;

(b) ligating adaptors to ends of the genomic fragments;

(c) removing excess adaptors that are not ligated to genomic DNA fragments in step (b);

(d) subjecting the genomic DNA-adaptor preparation so produced to a controllable initiating reaction for a PCR reaction in the presence of a first DNA primer and in the absence of a second DNA primer, wherein the first primer is complementary to a consensus sequence for the 3' end of Alu repeat sequences in the sample;

(e) subjecting the genomic DNA-adaptor preparation to a PCR amplification with said first DNA primer and a second DNA primer which is complementary to the adapter;

(f) digesting the products produced in the PCR amplification reaction of step (e) with restriction enzymes which recognize sequences in the DNA primers to generate DNA fragments with asymmetric overhangs; and (g) isolating highly polymorphic DNA subsets exhibiting selectively amplified sequences flanking 3' ends of Alu repeats produced in step (f).

3. A method according to claim 2 wherein homologous segments of selectively amplified sequences obtained in (f) are reannealed to obtain other subsets.

4. A method according to claim 2 wherein the restriction enzyme employed to digest genomic DNA generates GATC 5' overhangs.

5. A method according to claim 4 wherein the restriction enzyme is selected from the group consisting of Sau3AI, BstYI, and BamnHI.

6. A method according to claim 2 wherein the first primer is selected from the group consisting of GGGCGACA-GAGCGAAGACTCCGTCTCA (SEQ ID NO: 7), GGGC-GACAGCAGCGAGACTCCGTCTCA (SEQ ID NO: 2), and GGGCGACAGCAGCGAGACTCTGTCTCA (SEQ ID NO: 3).

7. A method according to claim 2 wherein the first primer has an extra base added to generate a site for a type IIS restriction enzyme.

8. A method according to claim 2 wherein the adaptors are TCTGGACCACTGTACGATGATATGTCACCGAG (SEQ ID NO: 4) and GATCCTCGGTG-cordycepin (SEQ ID NO: 5), and the second primer is TCTGGACCACTGTACGAT-GATATG (SEQ ID NO: 6).

9. A method according to claim 2 wherein the complexity of a subset generated is regulated by varying the annealing temperature during the initiating reaction.

10. A method according to claim 2 wherein the complexity of the subset generated is regulated by the recognition specificity of the first restriction enzyme.

11. DNA prepared according to a method of claim 6, 7, or 8.

12. A method of isolating DNA sequences from complex DNA sample pools, where allele frequency differs between the pools, comprising (a) mixing at least two different complex DNA samples together to generate a pool;

(b) ligating specific adaptors to DNA fragments in the pool;

(c) removing excess adaptors that are not ligated to the DNA fragments;

(d) mixing at least two different pools together;

(e) denaturing said mixed pools of DNA samples;

(f) reannealing said denatured pools of DNA samples to obtain DNA duplexes containing homologous strands;

(g) separating perfectly matched DNA duplexes in the pools from duplexes containing mismatched base pairs or insertion/deletion loops; and (h) selectively amplifying either perfectly matched or mismatched DNA homoduplexes and heteroduplexes.

13. A method according to claim 12 wherein the mismatched duplexes in step (g) are purified by affinity binding to proteins recognizing mismatched DNA.

14. A method according to claim 13 wherein the proteins are selected from the group consisting of mutS, thymidine glycosylase, carboxy terminus of p53, and mixtures thereof.

15. A method according to claim 12 wherein the mismatched duplexes in step (g) are destroyed.

16. A method according to claim 15 wherein mismatched duplexes are destroyed with an enzyme that cuts DNA containing mismatched DNA or insertion/deletion loops.

17. A method according to claim 16 wherein the enzyme is selected from the group consisting of mung bean nuclease, S1 nuclease, and mixtures thereof.

18. A method of isolating DNA sequences from complex DNA sample pools, where allele frequency differs between the pools, comprising:

(a) mixing at least two different complex DNA samples together to generate a first pool and mixing at least two different complex DNA samples together to generate a second pool;

(b) ligating first specific adaptors to DNA fragments in the first pool and second specific adaptors to DNA fragments in the second pool;

(c) removing excess adaptors that are not ligated to the DNA fragments;

(d) denaturing each of said first and second pools of DNA samples;

(e) separately reannealing each of said denatured pools of DNA samples to obtain DNA duplexes containing homologous strands;

(f) separating perfectly matched DNA duplexes in each pool from duplexes containing mismatched base pairs or insertion/deletion loops; and (g) selectively amplifying either perfectly matched or mismatched DNA homoduplexes and heteroduplexes.

19. A method according to claim 12 wherein the specific adaptors in step (b) comprise 5' overhang adaptors and 3' adaptors, wherein the two most 3' nucleotides of the 3' adaptors are mismatched with respect to the 5' adaptors, and the 3' adaptors are methylated at specific residues to mediate resistance to digestion with specific restriction enzymes, wherein DNA duplexes in step (f) are extended with a 5' and 3' exo-free polymerase to generate primer binding sites at each end of heteroduplexes but not of homoduplexes wherein the DNA duplexes are digested with methylation-sensitive restriction enzymes to remove primer binding sites generated from duplexes not having 3' adaptors; and wherein heteroduplexes are selectively amplified in step (h) using primers specific for the primer binding sites generated at each end of the heteroduplexes.

20. A method according to claim 2 wherein the restriction enzymes of step (f) are BbsI or BbvI for fragment ends generated by digestion of the first primer sequence and MboI, BstYI, or BamHI for ends generated by digestion of the second primer sequence.

21. A method according to claim 12 wherein the specific adaptors in step (b) comprise 5' overhang adaptors and 3' adaptors, wherein the 3' adaptor anneals perfectly with the 5' adaptor on homoduplexes, and wherein the 3' adaptors do not anneal with 5' adaptors from the opposite genome or pools of genomes, and the 3' adaptors is methylated at specific residues to mediate resistance to restriction enzyme digestion; wherein DNA duplexes in step (f) are extended with a 5' and 3' exo-free polymerase to generate primer binding sites at each end of homoduplexes; wherein the DNA duplexes are digested with methylation-sensitive restriction enzymes to remove primer binding sites generated from duplex DNA not having 3' adaptors; and wherein homoduplexes are selectively amplified in step (h) by using 2 primers specific for primer binding sites generated at each homoduplex fragment end, wherein DNA in said homoduplexes originate from the same pool.

22. A method wherein amplified material formed by the method of claim 12 is further processed through the steps of
   (a) treating with methylasts to mediate resistance to enzyme digestion; then
   (b) mixing, denaturing, and reannealing to obtain DNA material;
   (c) separating the material to obtain perfectly matched and mismatched duplex DNA;
   and then
   (d) selectively recovering homo- or heteroduplex DNA by PCR amplification based on resistance of primer binding sites to digestion by methylation sensitive restriction enzymes.

23. A method according to claim 22 wherein mismatched duplexes in step (c) are destroyed.

24. A method according to claim 22 wherein fragments having allele frequency differences between the pools are detected by change in ratio between homo- and heteroduplexes according to the principle of inequality.

25. A method for selectively amplifying heteroduplexes or homoduplexes formed by the method of claim 12 comprising:
   (a) dividing the mixture into two pools;
   (b) ligating adaptors containing a nucleotide sequence comprising a restriction enzyme cleavage site to both ends of all the DNA in one pool;
   (c) ligating adaptors containing the same nucleotide sequence to both ends of all the DNA in the second pool, provided that the sequence has a methylated base in the restriction site that blocks recognition of the site with a restriction enzyme;
   (d) reannealing the DNA in both pools;
   (e) subjecting the pools to the restriction enzyme; and
   (f) amplifying the DNA in both pools.

26. A method whereby recovered homo- and heteroduplexes from claim 12, 19, 21, or 25 are labelled with different signals, pooled, and hybridized to arrayed libraries, arrayed libraries of selected subsets of genomic clones, or metaphase chromosomes.

27. The method of claim 26 wherein mismatched duplexes are destroyed and ratios of said signals are compared to identify areas on the arrayed libraries or metaphase chromosomes where the signals are not equal, said areas representing loci where an allele is not equally represented in the pools, thus representing an allele frequency difference.

* * * * *

UNITED STATES PATENT AND TRADEMARK OFFICE
CERTIFICATE OF CORRECTION

PATENT NO. : 6,506,562 B1
DATED : January 14, 2003
INVENTOR(S) : Sherman M. Weissman et al.

It is certified that error appears in the above-identified patent and that said Letters Patent is hereby corrected as shown below:

Title page,
Item [56], References Cited, FOREIGN PATENT DOCUMENTS,
-- WO 89 01526A 2/1989
WO 93 22457 11/1993
WO 95 01453 1/1995
WO 97 29211 8/1997
WO 99 36575 7/1999 -- has been added;
OTHER PUBLICATIONS, -- Lisitsyn et al., "Cloning the Differences Between Two Complex Genomes" Science, U.S., American Association Advancement of Science, Vol. 259, February 12, 1993, pages 946-951 -- has been added.

Signed and Sealed this

Eleventh Day of November, 2003

JAMES E. ROGAN
*Director of the United States Patent and Trademark Office*